(12) United States Patent
Zweymüller

(10) Patent No.: US 6,436,147 B1
(45) Date of Patent: Aug. 20, 2002

(54) HIP-JOINT ENDOPROSTHESIS SYSTEM

(75) Inventor: Karl Zweymüller, Wien (AT)

(73) Assignee: Plus Endoprothetik AG, Rotkreuz (CH)

( * ) Notice: Subject to any disclaimer, the term of this patent is extended or adjusted under 35 U.S.C. 154(b) by 0 days.

(21) Appl. No.: 09/599,663

(22) Filed: Jun. 22, 2000

(51) Int. Cl.$^7$ ................................................ A61F 2/32
(52) U.S. Cl. .................... 623/22.41; 623/23.31
(58) Field of Search ...................... 623/22.41, 22.21, 623/22.11, 22.15, 20.11, 20.15, 23.45, 23.23, 23.11, 23.3 C, 23.31; 606/62

(56) References Cited

U.S. PATENT DOCUMENTS

| | | | |
|---|---|---|---|
| 5,108,451 A | | 4/1992 | Forte |
| 5,156,627 A | * | 10/1992 | Amstutz et al. .......... 623/23.23 |
| 5,480,451 A | * | 1/1996 | Grundei et al. .......... 623/23.11 |
| 5,888,210 A | * | 3/1999 | Draenert .................. 623/23.23 |
| 6,168,632 B1 | * | 1/2001 | Moser et al. ............ 623/23.31 |

FOREIGN PATENT DOCUMENTS

| | | |
|---|---|---|
| DE | 0 032 165 B1 | 12/1983 |
| FR | 2 631 543 A1 | 5/1988 |
| FR | 2 666 737 A1 | 9/1990 |
| FR | 2 701 835 A1 | 2/1993 |

\* cited by examiner

*Primary Examiner*—Pedro Philogene
(74) *Attorney, Agent, or Firm*—Knobbe, Martens, Olson & Bear LLP

(57) ABSTRACT

Hip-joint endoprosthesis system with a plurality of, in particular leaflike, prosthesis shafts (1.1', 1.2') for anchoring in the femur, wherein each shaft expands substantially on all sides from a distal end (5) towards proximal and comprises an anchoring section with a shaft long axis ($A_S$) that merges medially with an arch (7.1', 7.2') that continues into a prosthesis neck (9.1', 9.2') with a prosthesis-neck axis ($A_H$), such that the shafts differ with respect to a reference-point distance ($A_1'$, $A_2'$, $A_3'$) between the shaft long axis and a reference point ($R_1'$, $R_2'$, $R_3'$) on the prosthesis neck axis, which identifies the position of the center point of a joint ball set onto the prosthesis neck, and such that that the length (l) of the projection of the overall extent of the prosthesis shaft from the distal end of the anchoring section to the reference point or to the proximal end of the prosthesis neck is the same in all prosthesis shafts.

7 Claims, 4 Drawing Sheets

HIP-JOINT ENDOPROSTHESIS SYSTEM

FIELD OF THE INVENTION

This application claims priority under 35 U.S.C. § 119 of German application DE 199 28 709.0, filed Jun. 23, 1999.

DESCRIPTION

The invention relates to a hip-joint endoprosthesis system according to the precharacterizing clause of Claim 1.

Hip-joint endoprostheses with a leaflike shaft are disclosed in the patent EP 0 032 165 B1.

In this known construction the shaft is tapered, expanding approximately conically on all sides along its long axis from the distal end over a distance of between about ⅔ and ¾ of the total length of the shaft, measured along the long axis. In this upper region the medial narrow side of the shaft extends outward from the cone in a continuously curving arch that ends in a collarlike projection. This projection separates a femoral anchoring section of the shaft from a prosthesis neck, which comprises a peg that tapers proximally and serves to receive a spherical joint head. The axis of the prosthesis neck intersects the long axis of the shaft at an angle that corresponds substantially to the angle between the neck and the long axis of the femur in a natural hip joint.

The known construction has proved useful in avoiding a so-called "closure rotation" during insertion of the prosthesis without needing to make the plane of resection at the neck of the femur too deep. This disadvantageous "closure rotation" consists in the following: because the leaf of a conventional prosthesis shaft must have a certain minimal thickness, during complete insertion of such a shaft into the femur the shaft often rotates owing to the multiple curvature of the proximal end of the femur, which causes a straight or even slightly curved object to be diverted away from the wall of the femoral bone.

In clinical practice it has been shown that for large groups of patients who require an artificial hip joint, whereas the overall length of prostheses (to be understood as a projection of the total extent of the prosthesis shaft from its distal end to the outermost end of the peg formed on the prosthesis neck) is substantially the same, because of individual anatomical peculiarities it is necessary both to employ prosthesis shafts with different dimensions and hence also to use different tools to prepare the femur for the implantation thereof. More detailed investigations have revealed that within such patient groups the anatomical differences reside mainly in a difference in the distance separating the point of rotation of the hip-joint ball from the long axis of the femur. The object of the present invention, as follows, derives from this finding.

SUMMARY OF THE INVENTION

The object of the invention is to disclose a hip-joint endoprosthesis system of this generic kind that provides a saving of time and cost during implantation, in particular during the work of preparing the bone for implantation of the prosthesis shaft.

This object is achieved by a hip-joint endoprosthesis system with the characteristics given in Claim 1.

The invention includes the essential idea of providing a hip-joint endoprosthesis system the length of which, with reference to the long axis of the prosthesis shaft, is substantially constant. This system has the considerable advantage that when preparing the femur for implantation, it is possible to work with a uniform rasped dimension for all prosthesis sizes within the system.

The invention further includes the idea that this constancy of overall length of the prosthesis shaft, combined with differently long prosthesis necks, can be achieved in one variant by altering the angle between the axis of the prosthesis neck and the long axis of the anchoring section, according to the length of the prosthesis neck. In another variant this angle (the so-called "CCD angle") is kept constant but an "offset" section is inserted into the prosthesis neck in its long direction, such that the amount of lateral offset to be provided is determined by the required length of the prosthesis neck, i.e. by the required distance between the long axis of the anchoring section and that point (the "reference point") in the region of the peg of the prosthesis neck that coincides with the central point or point of rotation of the subsequently attached joint ball. In principle a combination of the two variants is also possible.

The second variant is most appropriate for relatively great prosthesis neck lengths, for which it might be necessary to make the prosthesis neck angle disadvantageously small in order to ensure uniformity of the overall length of the prosthesis shafts within the system. In such cases the advantages obtained with the prosthesis-neck offset section counterbalance the possible disadvantages of the irregularity (a "kink") in the medial arch line associated with inserting the offset (which in some circumstances can result in highly stressed pressure sites in the corresponding region of the spongiosa). In the range of less great prosthesis neck lengths, however, from the current viewpoint the adjustment of CCD angle in accordance with the prosthesis neck length appears to be the preferred variant.

A further essential aspect consists in constructing the prosthesis neck such that it is flattened in cross section. Its cross-sectional configuration is thus in some degree matched to the leaflike cross section of the femoral anchoring section; the spectrum comprises more or less flat ellipses, rectangles with rounded corner regions, combinations of circular and straight sections, or the like. In particular in combination with above-mentioned variant of a prosthesis shaft having an offset in the long direction of the prosthesis neck, it is advantageous in special embodiments for the cross-sectional configuration to change along the length of the neck. For example, an originally elliptical cross section in the region of the medial arch can become circular proximal to the offset section, or the cross section of the ellipse can change. In another embodiment the neck cross section can be approximately rectangular distal to the axis offset point, whereas proximal to this point it is square or has a different rectangular shape.

In one special embodiment, advantageously matched to the anatomical relationships, the shaft cross section is approximately trapezoidal at least in the proximal section, in particular has a symmetrical trapezoidal shape with two equally long longer sides that in cross section delimit the anterior and posterior surfaces of the shaft, and two differently long shorter sides of which the shorter corresponds to the medial surface and the longer, to the lateral surface of the shaft.

Additional advantageous structural features and alternatives of the construction in accordance with the invention will be apparent from the subordinate claims and are described in detail with reference to the following exemplary embodiments and to the attached drawings, wherein:

DETAILED DESCRIPTION OF THE INVENTION

Figure 1:
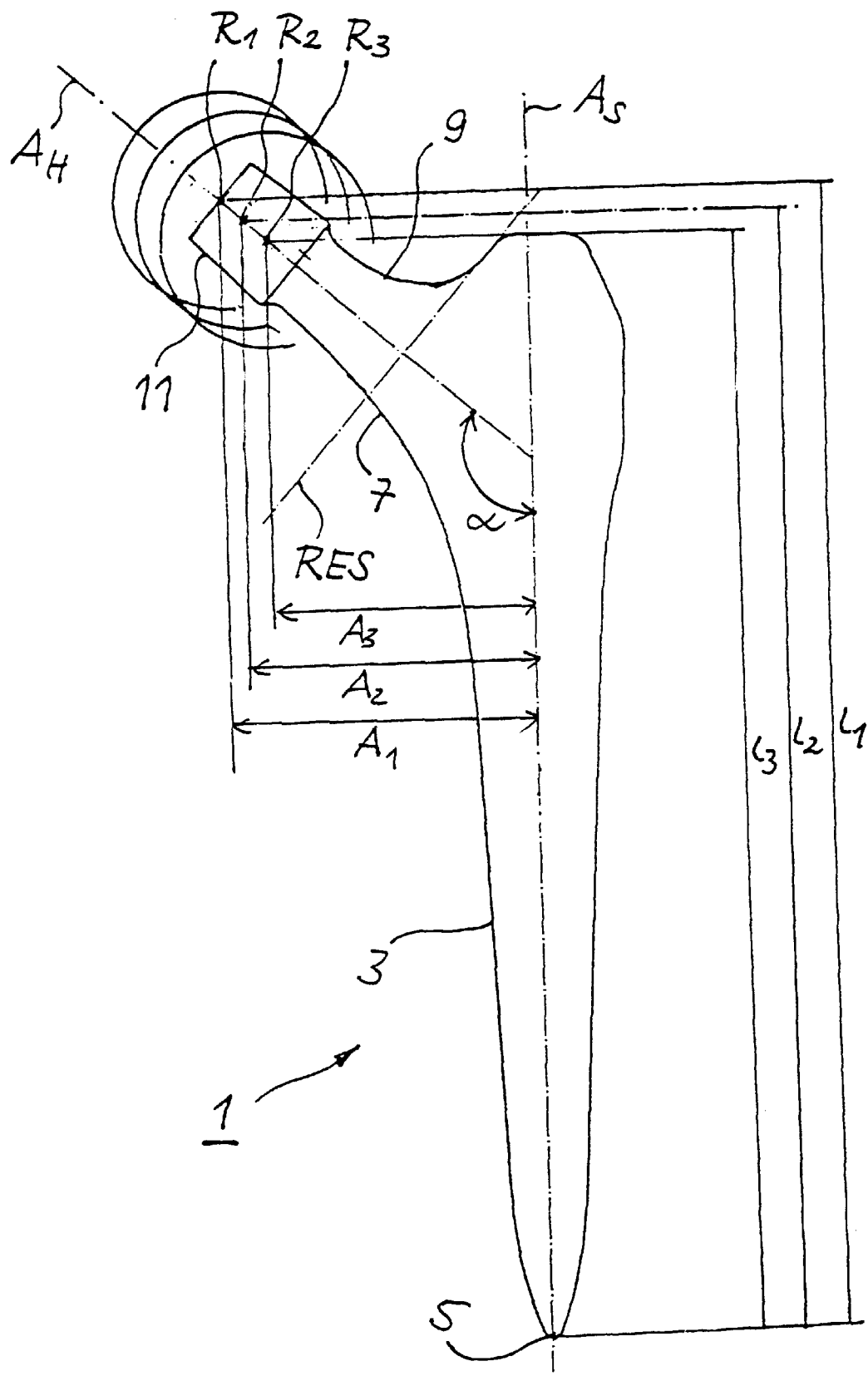
FIG. 1 is a side view of a leaflike shaft prosthesis in which are sketched possible positions of various joint balls with differently long neck sections, showing the corresponding reference points and distances from the long axis of the shaft.

A prosthesis shaft 1 shown in FIG. 1 serves to anchor a hip-joint prosthesis in the femur. Starting at a distal end 5, the prosthesis shaft 1 expands approximately uniformly on all sides towards the proximal region, where it is continuous by way of a medial arch 7 with a prosthesis neck 9 that ends proximally in a peg 11 to receive a joint ball. The position of an anchoring section 3 of the prosthesis shaft 1 can be described by a shaft long axis $A_S$, whereas the position of the prosthesis neck can be described by its long axis $A_H$. The shaft long axis $A_S$ and the neck axis $A_H$ enclose an angle $\alpha$ (customarily called the CCD angle). In FIG. 1 the resection plane RES to which reference is made during implantation is also indicated.

As sketched in the figure, within a given shaft system the various prosthesis shafts of the kind shown here can have necks of different lengths and hence—assuming a constant CCD angle $\alpha$—can differ with respect to the distances $A_1$, $A_2$, $A_3$ between shaft long axis $A_S$ and the associated reference points $R_1$, $R_2$, $R_3$, respectively, in the region of the peg 11. Each of the reference points $R_1$, $R_2$, $R_3$ designates the center point of an associated joint ball (which is not identified by a special symbol in the figure). The individual prostheses in the system thus also differ in their overall length, i.e. the distance between the distal end 5 and the individual reference point $R_1$, $R_2$, or $R_3$, which in the figure is identified by $l_1$, $l_2$ or $l_3$, respectively. As a result, during preparation of the femur different rasped dimensions must be used, so that if the number of patients to be treated is relatively large, a relatively great amount of effort must be expended for such preparation.

Figure 2A:
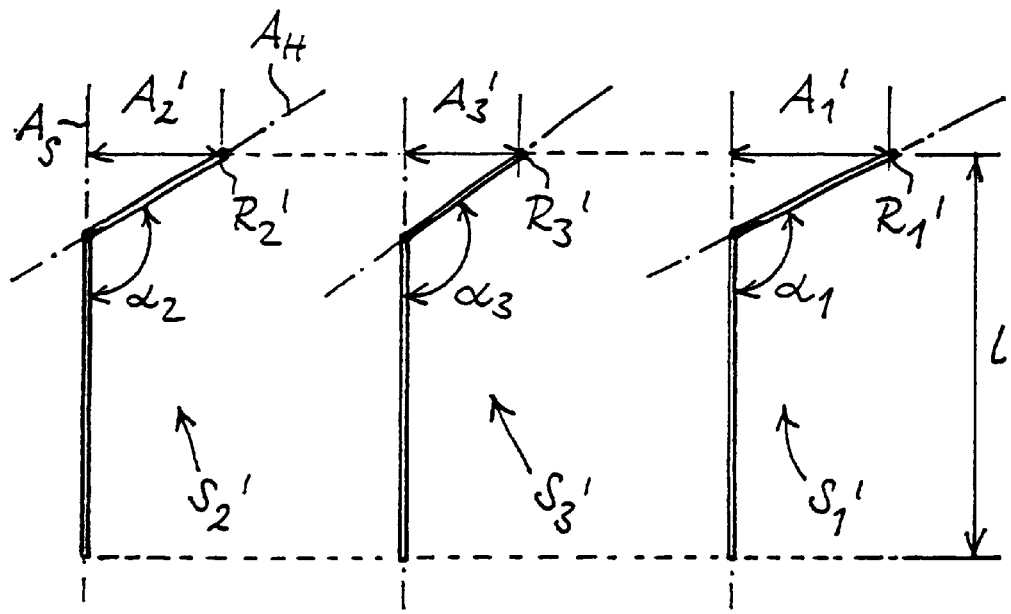
FIG. 2a is a schematic drawing to explain a first embodiment of the invention.

FIG. 2a is a set of diagrams representing a first variant of the embodiment of the invention, which is characterized by the provision of different CCD angles $\alpha_1$, $\alpha_2$ or $\alpha_3$ in the prosthesis shafts $S_1'$, $S_2'$ and $S_3'$, respectively, of a hip-joint endoprosthesis system (in this case a three-part system). The variation of the CCD angle between the shaft long axis $A_S$ and the neck axis $A_H$ enables all the prosthesis shafts to have the same overall length l despite the different distances $A_1$, $A_2$, $A_3$ between the shaft long axis $A_S$ and the associated reference point $R_1'$, $R_2'$, $R_3'$.

Figure 2B:
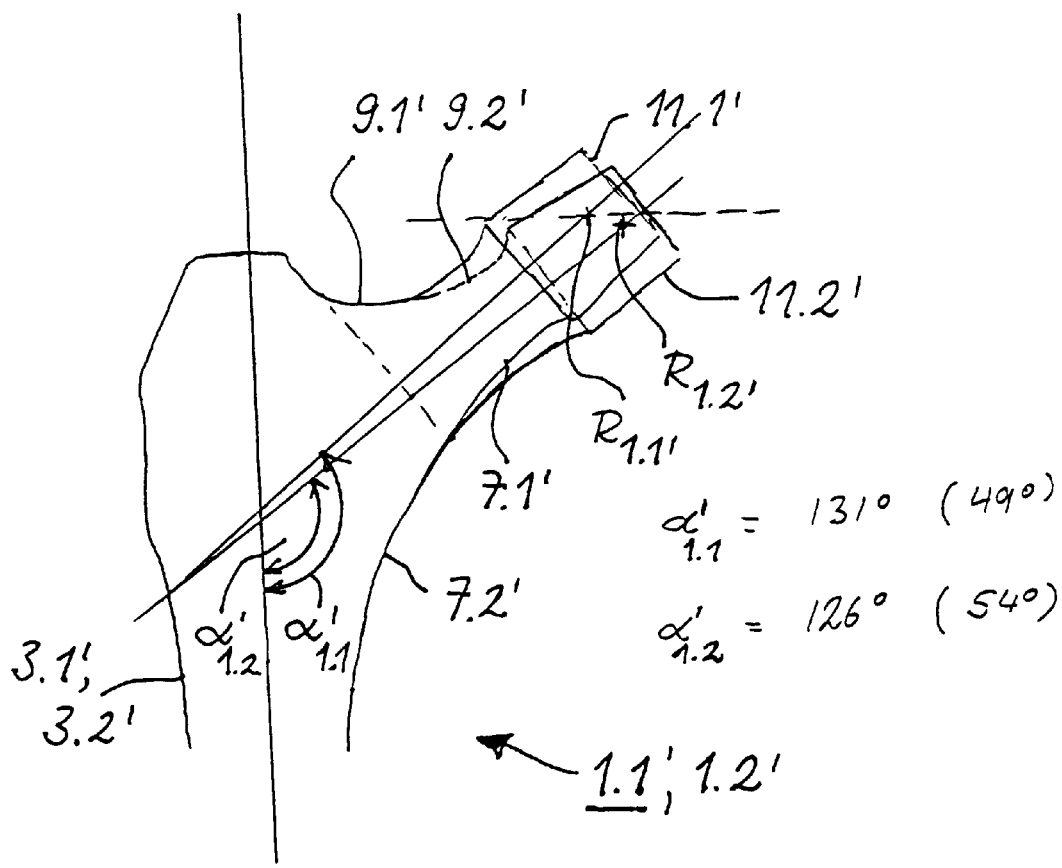
FIG. 2b is a partial view of two superimposed prosthesis shafts with which this embodiment is implemented.

In FIG. 2b this embodiment is shown in somewhat greater detail, in a partial view of a leaflike prosthesis shaft of the kind shown in FIG. 1. In a superimposed, sketch-like representation the figure shows the proximal region of two prosthesis shafts 1.1' and 1.2'. The anchoring sections of these prosthesis shafts, labelled 3.1' and 3.2', respectively, are identical in their external contours; however, the inclinations of the prosthesis necks 9.1' and 9.2', beginning as far distal as the region of the medial arch 7.1' or 7.2', and the positions of the pegs 11.1' and 11.2' are different. The projections of the associated reference points $R_{1.1'}$ and $R_{1.2'}$ with respect to the shaft long axis $A_S$ are effectively made to coincide in that the CCD angle $\alpha'_{1.1}$ of the prosthesis shaft 1.1' is set at a value of 131° and the CCD angle $\alpha'_{1.2}$ of the prosthesis shaft 1.2' is set at a value of 126°. Of course, this difference in angle brings about the divergent contour, visible in the figure, in the region including the distal end of the medial arch and the prosthesis neck as a whole.

Figure 3:
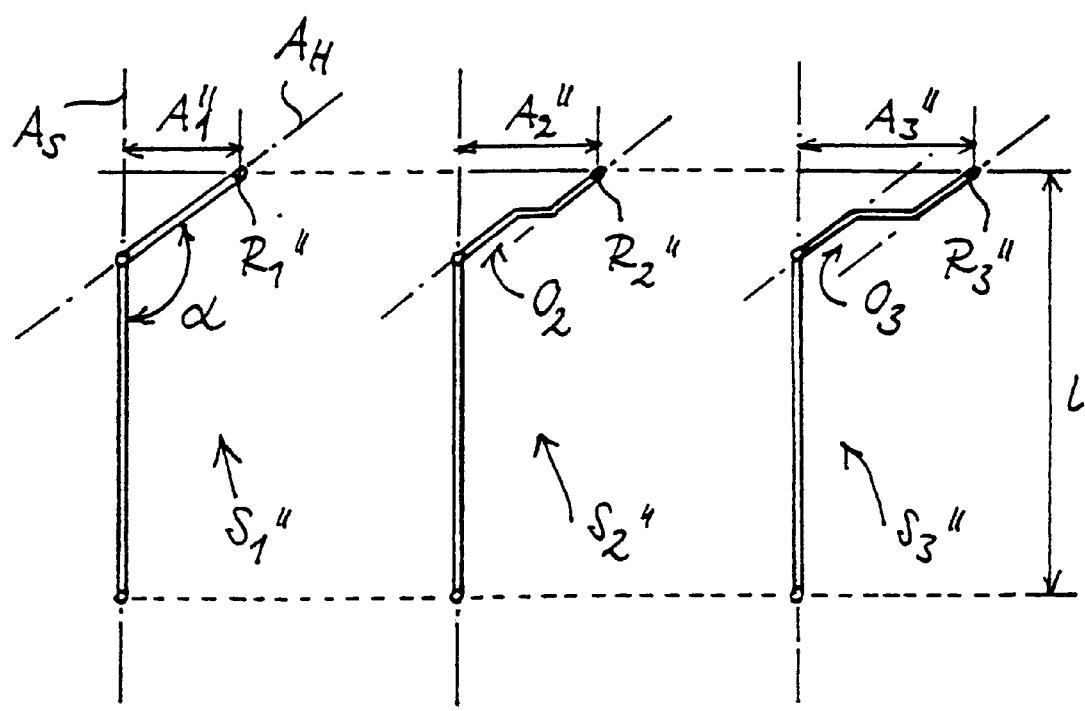
FIG. 3 is a schematic drawing to explain a second embodiment of the invention, and in FIGS. 4a–4d various prosthesis-neck cross sections are sketched.

In FIG. 3 and alternative embodiment of the invention is shown by means of rough diagrams of three prosthesis shafts $S_1''$, $S_2''$ and $S_3''$. The special feature of this embodiment consists in the provision of an offset $O_2$ or $O_3$ in the course of the neck of the prosthesis shafts $S_2''$ and $S_3''$, respectively. This offset enables the overall length l of all prosthesis shafts in the system to be made the same, in spite of the different distances between the reference points $R_1''$, $R_2''$ or $R_3''$ and the shaft long axis $A_S$, and despite the uniform angle $\alpha$ between $A_S$ and the neck axis $A_H$.

In FIGS. 4a to 4d are shown in cross section—merely as examples of the diversity of possible concrete cross-sectional shapes—some preferred embodiments of the prosthesis neck 9.1' or 9.2' of a hip-joint prosthesis shaft such as is represented in FIG. 2b. To distinguish these from one another and from the prosthesis neck according to FIG. 2b (assumed to be circular in cross section), the prosthesis necks in thise drawings are identified as 9A, 9B, 9C and 9D.

Figure 4A:
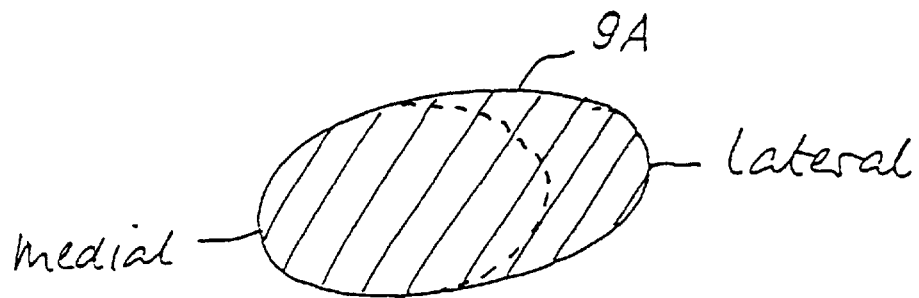
Figure 4B:
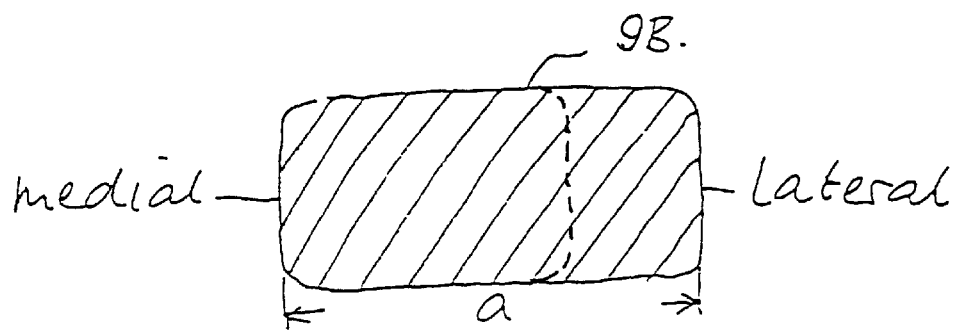
Figure 4C:
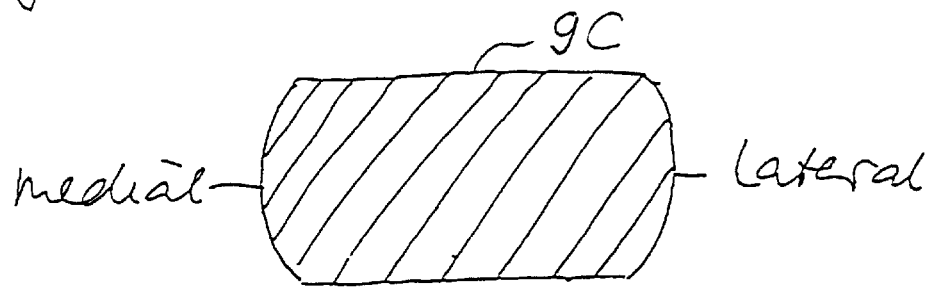
Figure 4D:
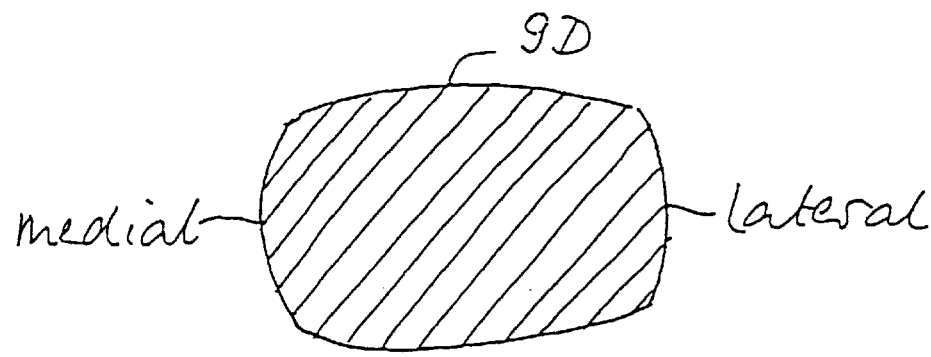

In the embodiment according to FIG. 4a the anterior-posterior flattening produces an elliptical cross section, such that the major axis of the ellipse is oriented substantially in the medial-lateral direction. FIG. 4b shows another variant, in which the prosthesis neck has the cross section of a rectangle rounded in the corner regions. The longer side of the rectangle a here extends—in analogy to the major axis of the ellipse according to FIG. 4a—in the medial-lateral direction. In the embodiment shown in FIG. 4c the anterior and posterior boundaries of the cross-sectional shape are straight lines, whereas the medial and lateral boundary lines are each sections of a circular arc. The prosthesis neck 9D shown in FIG. 4 has a cross-sectional shape in which all the boundary lines are sections of circular arcs, those that form the anterior and posterior boundaries having a larger radius than those that form the medial boundary.

In FIGS. 4a and 4b a dashed line in each drawing indicates the surface contour of the corresponding prosthesis neck 9A or 9B proximal to an offset point such as exists in prosthesis shafts of the system sketched in FIG. 3. In such an embodiment, therefore, the neck cross section in the region proximal to the offset section differs from that in the region distal to this section, which can advantageously enable the surface contour to be made uniform in the region of the medial arch in all shafts of the system, even though a more or less large offset is present in individual prostheses.

The cross section of the anchoring section of the prosthesis shafts in the embodiments proposed here can have the shapes already known for leaflike prosthesis shafts; however, the proposed solution can be implemented especially advantageously with a substantially trapezoidal shaft cross section, which is especially well suited to the anatomical situation. The shape of this trapezoid is preferably substantially symmetrical, the anterior and posterior edges being equally long and longer than the lateral and medial edges, of which in turn the medial edge is the shorter. In the edge regions of the corresponding anchoring section (i.e., at the corners of the trapezoid that specifies the cross-sectional shape) chamfers or facets are preferably provided.

All the characteristics disclosed in the application documents are claimed as essential to the invention insofar as

| List of reference numerals | |
| --- | --- |
| 1; 1.1', 1.2' | Prosthesis shaft |
| 3; 3.1', 3.2' | Anchoring section |
| 5 | Distal end |
| 7; 7.1', 7.2' | Medial arch |
| 9; 9.1', 9.2', 9A, 9B, 9C, 9D | Prosthesis neck |
| 11; 11.1', 11.2' | Peg |
| $A_S$ | Long axis of shaft |
| $A_W$ | Axis of neck |
| $A_1, A_2, A_3; A_1', A_2', A_3'; A_1'', A_2'', A_3''$ | Distance between long axis of shaft and reference point |
| $1, 1_1, 1_2, 1_3$ | Shaft length |
| $R_1, R_2, R_3; R_1', R_2', R_3'; R_1'', R_2'', R_3''$ | Reference point |
| RES | Resection plane |
| $S_1', S_2', S_3', S_1'', S_2'', S_3''$ | Prosthesis shaft |
| $\alpha, \alpha_1, \alpha_2, \alpha_3; \alpha'_{1.1}, \alpha'_{1.2}$ | CCD angle |

What is claimed is:

1. A hip-joint endoprosthesis system comprising a plurality of prosthesis shafts for anchoring in the femur, wherein each shaft expands substantially on all sides from a distal end towards a proximal end and wherein each shaft comprises:

an anchoring section comprising a shaft long axis that merges medially with an arch and continues into a prosthesis neck; and a prosthesis neck axis, wherein the shafts differ with respect to a reference-point distance between the shaft long axis and a reference point on the prosthesis neck axis, which identifies the position of the center point of a joint ball set onto the prosthesis neck, wherein the length of the projection of the overall extent of the prosthesis shaft from the distal end of the anchoring section to the reference point or to the proximal end of the prosthesis neck is the same in all prosthesis shafts, and wherein in the prosthesis shafts with different reference-point distances, a prosthesis-neck angle between the shaft long axis and the prosthesis-neck axis is specified differently, depending on the reference-point distance.

2. The hip-joint endoprosthesis system according to claim 1, wherein the maximal extend of the prosthesis neck transverse to the prosthesis-neck axis in at least a subsection of its longitudinal course is less in the anterior-posterior direction than the maximal extent in the medial-lateral direction.

3. The hip-joint endoprosthesis system according to claim 2, wherein the cross-section of the prosthesis neck in at least a subsection of its extent is substantially elliptical or rectangular or comprises at least one straight and one curved boundary line.

4. The hip-joint endoprosthesis system according to claim 1, wherein the course of a medial arch line that connects the anchoring section to the prosthesis neck is identical at least over the greatest part of its length in all prosthesis shafts.

5. The hip joint endoprosthesis of claim 1 wherein said prosthesis shafts are leaflike.

6. A hip-joint endoprosthesis system comprising a plurality of prosthesis shafts for anchoring in the femur, wherein each shaft expands substantially on all sides from a distal end towards a proximal end and wherein each shaft comprises:

an anchoring section comprising a shaft long axis that merges medially with an arch and continues into a prosthesis neck; and a prosthesis neck axis, wherein the shafts differ with respect to a reference-point distance between the shaft long axis and a reference point on the prosthesis neck axis, which identifies the position of the center point of a joint ball set onto the prosthesis neck, wherein the length of the projection of the overall extent of the prosthesis shaft from the distal end of the anchoring section to the reference point or to the proximal end of the prosthesis neck is the same in all prosthesis shafts, and wherein in at least one of the prosthesis shafts with different reference-point distances, there is provided, in the longitudinal course of the prosthesis neck, an axis offset in the distal direction, the magnitude of which is specified in dependence on the reference-point distance.

7. The hip-joint endoprosthesis system according to claim 6, wherein the cross-section of the prosthesis neck in a region distal to the axis offset point is formed differently from the cross-section in a region proximal to the axis offset point.

* * * * *